United States Patent [19]

Watanabe et al.

[11] Patent Number: 4,486,418
[45] Date of Patent: Dec. 4, 1984

[54] 2'-DEAMINO AMINOGLYCOSIDES AND COMPOSITION THEREOF

[75] Inventors: Isamu Watanabe; Takashi Yamaguchi; Kazuhiro Kamiya; Toshihito Mori, all of Higashimurayama, Japan

[73] Assignee: Kowa Company, Ltd., Nagoya, Japan

[21] Appl. No.: 501,392

[22] Filed: Jun. 6, 1983

[30] Foreign Application Priority Data

Jun. 4, 1982 [JP] Japan ................................. 57-94900

[51] Int. Cl.³ ...................... A61K 31/71; C07H 15/22
[52] U.S. Cl. .................................. 424/180; 536/16.1; 536/16.8
[58] Field of Search .............. 536/16.1, 16.8; 424/180

[56] References Cited

U.S. PATENT DOCUMENTS 4,214,075  7/1980  Tadanier et al. .................. 536/16.1
4,251,516  2/1981  Martin et al. .................... 536/16.1

FOREIGN PATENT DOCUMENTS 2855350  7/1979  Fed. Rep. of Germany ..... 536/16.1

OTHER PUBLICATIONS

March, *Advanced Organic Chemistry*, 2nd ed., (1977), p. 404.

*Primary Examiner*—Johnnie R. Brown
*Assistant Examiner*—Elli Peselev
*Attorney, Agent, or Firm*—Wenderoth, Lind & Ponack

[57] ABSTRACT

An aminoglycoside represented by the following formula (1)

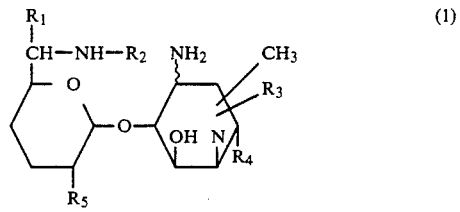

wherein each of $R_1$ and $R_2$ represents a hydrogen atom or a methyl group, $R_3$ represents a hydrogen atom or an aminoacyl group, $R_4$ represents a hydrogen atom or a hydroxyl or methoxy group, and $R_5$ represents a hydrogen atom or a hydroxyl group, or a pharmaceutically acceptable acid addition salt thereof, a process for the production thereof and a pharmaceutical use thereof.

3 Claims, No Drawings

2'-DEAMINO AMINOGLYCOSIDES AND COMPOSITION THEREOF

This invention relates to novel aminoglycosides having a hydrogen atom or a hydroxyl group in the 2'-position which are derived from known aminoglycosides having an NH$_2$ group at the 2'-position, a process for production thereof, and use thereof.

More specifically, this invention relates to an aminoglycoside of the following formula (1)

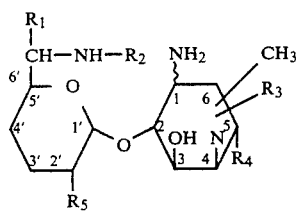

wherein each of $R_1$ and $R_2$ represents a hydrogen atom or a methyl group, $R_3$ represents a hydrogen atom or an aminoacyl group, $R_4$ represents a hydrogen atom or a hydroxyl or methoxy group, and $R_5$ represents a hydrogen atom or a hydroxyl group, or a pharmaceutically acceptable acid addition salt thereof.

This invention also provides a process for producing the compounds of formula (1) or their pharmaceutically acceptable acid addition salts from known aminoglycosides of the following formula (2)

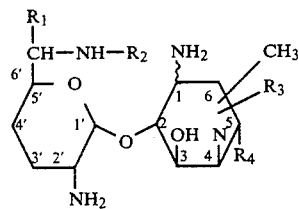

wherein $R_1$, $R_2$, $R_3$ and $R_4$ are as defined above.

The invention further relates to uses of the compounds of formula (1) as antibiotics.

We have found that compounds of formula (1) in which the 2'-position is deaminated and compounds of formula (1) in which —OH group is at the 2'-position, which are not described in the known literature, can be produced advantageously in good yields by any easy method from known aminoglycosides of formula (2) in which NH$_2$ is at the 2'-position, and that the compounds of formula (1) have antibiotic activity comparable to the compounds of formula (2) and exhibit better antibiotic activity against resistant bacteria. It has further been found that the compounds of formula (1) have low toxicity.

It is an object of this invention to provide novel compounds useful as antibiotics, a process for production thereof and use thereof.

The above and other objects and advantages of this invention will become more apparent from the following description.

The starting aminoglycosides used to produce the compounds of formula (1) are expressed by the following formula (2).

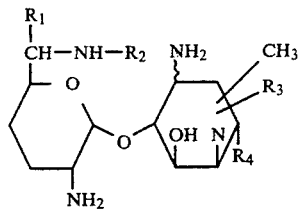

wherein $R_1$ and $R_2$ each represent a hydrogen atom or a methyl group, $R_3$ represents a hydrogen atom or an aminoacyl group, and $R_4$ represents a hydrogen atom or a hydroxyl or methoxy group.

The compounds of formula (2) are known antibiotics called KA-6606, KA-7038, and their derivatives. Their structures, manufacturing processes and uses are described, for example, in U.S. Pat. Nos. 4,206,206 and 4,328,307 (also the corresponding German OLS No. 2813021), U.S. Pat. Nos. 4,312,858 and 4,329,426 (also the corresponding west German Patent No. 2928373), U.S. Pat. No. 4,255,421 (also the corresponding west German OLS No. 2942194), and U.S. Pat. No. 4,353,893.

The novel aminoglycosides of this invention represented by the following formula (1)

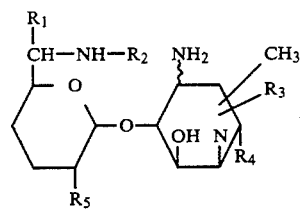

wherein each of $R_1$ and $R_2$ represents a hydrogen atom or a methyl group, $R_3$ represents a hydrogen atom or an aminoacyl group, $R_4$ represents a hydrogen atom or a hydroxyl or methoxy group, and $R_5$ represents a hydrogen atom or a hydroxyl group, or a pharmaceutically acceptable acid addition salt thereof can be produced, for example, by the following process (a), (b) or (c).

In the above formula (1), the aminoacyl group for $R_3$ may, for example, be an aminoacyl group having 2 to 4 carbon atoms in the acyl moiety. Specific examples are glycyl, alanyl, β-alanyl, valyl and sarcosyl groups.

Process (a)

This process comprises oxidizing the compound of formula (2) in which amino groups other than the 2'-amino group, i.e. the amino group at the 1-position and/or the 4-position and/or 6'-position, are protected by protective groups, with an oxidizing agent, hydrolyzing the oxidation product, reducing the product thus obtained, and then splitting off the protective groups, optionally followed by acylation. If desired, the product is contacted with a pharmaceutically acceptable acid to convert it into its pharmaceutically acceptable acid addition salt.

The compound of formula (2) in which amino groups other than the 2'-amino group are protected by protective groups can be produced by methods known per se.

Since in the compound of formula (2), the 2'-amino group is more reactive with conventional amino group-protecting reagents than the amino groups at the other positions, it is preferred to first protect the 2'-amino group by a suitable protective group, then protect the amino groups at the other positions by other protective groups which can be split off under different conditions from those used to split off the first-mentioned protective group, and then to split off the protective group for the 2'-amino group. In protecting the 2'-amino group, the protecting reagent is used preferably in an amount of nearly one equivalent.

Specific examples of the method for producing the compound of formula (2) in which amino groups other than the 2'-amino group are protected by protective groups include (1) a method involving protecting the 2'-amino group by a benzyloxycarbonyl group and the other amino groups by acetyl groups, (2) a method involving protecting the 2'-amino group by a p-methoxybenzyloxycarbonyl group and the other amino groups by benzyloxycarbonyl groups, and (3) a method involving protecting the 2'-amino group by a t-butoxycarbonyl group and the other amino groups by benzyloxycarbonyl groups.

The reaction conditions for the protection of the amino groups are known and can be properly chosen. For example, one equivalent of a protecting reagent for the 2'-amino group is added in a solvent such as methanol, ethanol, water, dioxane or a mixture thereof in the presence or absence of a divalent metal acetate such as nickel acetate, zinc acetate or cobalt acetate, and the reaction is carried out at 0° C. or below for 1 to 30 hours. The product is purified and thereafter in a similar solvent, a protective reagent for the other amino groups is added. The mixture is stirred at 0° C. to room temperature for 0.5 to 30 hours.

When a compound of formula (1) in which $R_4$ is a hydrogen atom is to be produced from a starting compound of formula (2) in which $R_4$ is a hydroxyl group, it is possible to protect the amino groups as described above, then protect the hydroxyl group at the 3-position by, for example, forming a cyclic carbamate with the 4-amino group, split off the hydroxyl group at the 5-position, and then split off the protective group for the 2'-amino group, thereby forming the compound of formula (2) in which the amino groups other than the 2'-amino group are protected by protective groups.

By oxidizing the compound of formula (2) thus formed in which the amino groups other than the 2'-amino group are protected, with an oxidizing agent, —$NH_2$ at the 2'-position can be converted to =NOH. By hydrolysis, =NOH can be converted to =O. Subsequently, by reduction, =O can be converted to —OH. Thus, the compound of formula (1) in which —OH is at the 2'-position can be produced. When $R_3$ is the resulting compound of formula (1) is H, it can be acylated, as desired, to convert $R_3$ into an aminoacyl group.

Examples of suitable oxidizing agents used in the above oxidation reaction include benzoquinones such as 3,5-di-t-butyl-1,2-benzoquinone and 3,5-di-isopropyl-1,2-benzoquinone; dialdehydes such as mesityl glyoxal, 3-nitromesityl glyoxal, 3,5-dinitromesityl glyoxal and 3,5-dichloromesityl glyoxal; and peroxides such as hydrogen peroxide, peracetic acid and perbenzoic acid.

The oxidation reaction can be carried out in a solvent such as water, methanol, ethanol, or dioxane in the presence or absence of a catalyst at a temperature of, for example, —10° to 100° C., for a period of, for example, several minutes to 20 hours. Examples of the catalyst are triethylamine, 1,5-diazabicyclo [4.3.0] nona-5-ene, alkali alkoxides, sodium tungstate, and potassium tungstate.

Hydrolysis of the resulting compound can give a 2'-deamino-2'-oxo compound. Preferably, the hydrolysis is carried out under acidic conditions in the presence of, for example, an organic acid such as oxalic acid, levulinic acid, malonic acid and succinic acid, an inorganic acid such as sulfurous acid, nitrous acid, hydrochloric acid, sulfuric acid or nitric acid, or a salt of such an organic or inorganic acid. The reaction can be carried out at a temperature of, for example, 0° to 100° C. for a period of, for example, 1 to 50 hours.

The production thus obtained is then reduced to obtain a compound in which the hydroxyl group is at the 2'-position.

Means for reduction can be properly chosen. Preferably, the reduction is carried out by using reducing agents. Examples of such reducing agents are lithium aluminum hydride, sodium borohydride, hydrogen iodide and hydrogen sulfide. The reduction can be carried out, for example, by adding a reducing agent to the hydrolysis product in a solvent such as water, methanol or ethanol and stirring the mixture at a temperature of, for example, 0° to 50° C. for a period of, for example, 0.1 to 20 hours.

The free compound of formula (1) can be obtained by eliminating the protective groups of the resulting compound of formula (1) in which 1 to 4 amino groups are protected. Deprotection can be effected by techniques known per se, preferably by a catalytic reducing method and an acid decomposition method. The catalytic reduction can be carried out, for example, by reducing the product with hydrogen in a suitable solvent in the presence of a suitable reducing catalyst. The reducing catalyst is preferably one composed of a metal of Group VIII of the periodic table such as palladium, platinum, Raney nickel, rhodium, ruthenium and nickel. The solvent may be the same as those exemplified hereinabove. The reaction conditions can be properly selected. For example, the hydrogen pressure is about 1 to about 5 atmospheres, the reaction temperature is about 0° to about 100° C., and the reaction time is about 0.1 to about 10 hours.

The acid decomposition can be carried out by decomposing the product with a suitable acid in a suitable solvent. Examples of acids that can be used are hydrochloric acid, hydrobromic acid or hydrofluoric acid. Examples of the solvent are acetic acid, methanol, ethanol, dioxane, and water. The reaction conditions can be suitably selected. For example, the reaction temperature is 0° to 100° C., and the reaction time is 0.1 to 10 hours.

When an acyl group such as an acetyl group is used as a protective group for the amino group, deprotection can be carried out by alkaline hydrolysis. This hydrolysis can be carried out, for example, by stirring the compound in an alkali hydroxide (e.g. 1 to 4N) at a temperature of, for example, 50° to 100° C. for a period of, for example, 1 to 20 hours.

If desired, the compound of formula (1) in which the 2'-position is —OH and the 4-position is a methylamino group ($R_3$=H) can be acylated to convert it to a compound of formula (1) in which $R_3$ is an aminoacyl group. The acylation can be carried out, for example, in accordance with the methods disclosed in U.S. Pat. Nos. 4,255,421 and 4,353,893 cited above. Specifically, the compound of formula (1) in which the 4-position is a methylamino group and the amino groups other than the 4-position are protected with protective groups is subjected to the action of a suitable acylating agent, and then the protective groups are split off.

Protection of the amino groups other than the 4-position can be performed, for example, by selectively protecting the 1- and 6'-positions by using an active ester of benzyloxycarboxylic acid, preferably its substituted phenyl ester, N-hydroxysuccinimide ester or N-hydroxyphthalimide ester. Furthermore, when the methylamino group at the 4-position is simultaneously protected as mentioned hereinabove, the methylamino group at the 4-position alone can be selectively converted to a free amino group by forming a cyclic carbamate between the hydroxyl group at the 3-position and the methylamino group at the 4-position and then hydrolyzing the cyclic carbamate. Or the methylamino group at the 4-position can be directly converted to a free amino group by the action of an alkali on the tetra-N-protected compound of formula (1) in a solvent containing water, as described hereinabove.

Splitting off of the protective groups can be carried out by catalytic reduction or acid hydrolysis as described above.

Acylation of the 4-methylamino group can be performed, for example, by using a conventional peptide synthesizing technique. Acylation is carried out by using an amino-protected amino acid or another substituted carboxylic acid or a reactive derivative thereof. Examples of the reactive derivative are acid halides, active esters such as phenyl ester, cyanomethyl ester, N-oxysuccinimide ester or N-oxyphthalimide ester, acid azides, acid anhydrides, mixed acid anhydrides, and other compounds which are used in the synthesis of peptides. Protective groups for the amino group of the amino acid may be the same as those exemplified hereinabove for the amino or methylamino groups of the compound of formula (1) in which $R_3$ is hydrogen. Preferably, quite the same protective groups should be used.

The acylation reaction can be performed, for example, at a temperature of about 0° to about 100° C. in a solvent such as methanol, dioxane, acetonitrile and dichloromethane by using about 1 to about 10 moles of an acylating agent per mole of the compound to be acylated. Usually, the reaction can be terminated in about 0.5 to about 20 hours.

Examples of acylating agents used in the acylating reaction are amino acids such as glycine, alanine, β-alanine, valine and sarcosine, in which the amino groups are protected. The amino groups of these amino acids may be substituted, for example, by a lower alkyl group, a carbamoyl group, a formyl group, or a formimidoyl group.

Process (b)

This process comprises treating the compound of formula (2) in which the amino groups other than the 2'-amino group, i.e. the amino groups at the 1- and/or 4-and/or 6'-position, are protected by protective groups, with a formylating agent to convert it into a compound in which the 2'-position in a formylamino group (—NHCHO), dehydrating the compound to form a compound in which the 2'-position is isonitrile (—NC), reducing the product thus obtained to give a compound (1) in which $R_5$ is a hydrogen atom, and then splitting off the protective groups, optionally followed by acylation. If desired, the product is contacted with a pharmaceutically acceptable acid to convert it into a pharmaceutically acceptable acid addition salt.

Formylation of the 2'-amino group of the compound of formula (2) in which the amino groups other than the 2'-amino group are protected and which can be obtained as described with regard to process (a) can be performed by subjecting the aforesaid compound to the action of a formylating agent such as a mixed anhydride of formic acid and acetic acid, an active ester of formic acid such as N-hydroxysuccinimide ester of formic acid. Formylation can be carried out by adding the formylating agent in a solvent such as ether or tetrahydrofuran, and stirring the solution at a temperature of, for example, 0° to 50° C. for a period of, for example, 0.1 to 10 hours.

Dehydration treatment of the compound in which the 2'-position is a formylamino group can be carried out, for example, by contacting it with a suitable dehydrating agent such as phosphorus oxychloride or p-toluenesulfonyl chloride in the presence of a suitable organic base such as triethylamine or pyridine. Specifically, it can be carried out, for example, by adding the base and the dehydrating agent in a solvent such as dichloromethane or chloroform and stirring the mixture at −60° to 50° C. for 1 to 20 hours.

Reduction of the product thus obtained can be carried out by a suitable known means. For example, it can be performed by a method which comprises reacting the resulting compound in which the 2'-position is isonitrile with a trialkylstannane preferably tri-n-butylstannane, a method which comprises reacting the above compound with an alkali metal such as lithium, sodium or potassium in liquid ammonia or tetrahydrofuran, or a method which comprises reacting the above compound with sodium and naphthalene.

In the first embodiment cited above, it is possible to add a small amount of a radical initiator such as azobisisobutyronitrile and tri-n-butyl-stannane in a solvent such as benzene and toluene and stir the mixture at a temperature of, for example, 0° to 150° C. for a period of, for example, 1 to 30 hours. In the second embodiment cited above, it is possible to add an alkali metal in liquid ammonia or liquid methylamine, and to stir the mixture of about −100° C. to about 0° C. for about 0.1 to about 5 hours. In the third embodiment cited above, it is possible to add a sodium naphthalane solution in a solvent such as tetrahydrofuran or 1,2-dimethoxyethane under an argon or nitrogen atmosphere at about −20° C. to room temperature and to stir the mixture at the same temperature for about 0.1 to about 5 hours.

The resulting compound of formula (1) in which $R_5$ is a hydrogen atom can be deprotected in the same way as described above with regard to process (a).

Compounds of formula (1) in which the 2'-position is H and the 4-position is a methylamino group ($R_3=H$) can be converted, if desired, to a compound of formula (1) in which $R_3$ is an acyl group by acylating it.

Process (c)

This process comprises subjecting the compound of formula (2) in which the amino groups other than the 2'-amino group are protected by protective groups and which can be obtained as described with regard to process (a) to the action of hydroxylamine-O-sulfonic acid ($NH_2O-SO_3H$) to deaminate it directly, and then splitting off the protective groups, optionally followed by acylation. If desired, the resulting product can be converted to its pharmaceutically acceptable acid addition salt by contacting it with a pharmaceutically acceptable acid.

The above deamination can be carried out, for example, by subjecting the compound of formula (2) in which the amino groups other than the 2'-amino group are protected to the action of for example about 2 to about 5 equivalents, per equivalent of the compound of formula (2), of hydroxylamine-O-sulfonic acid in the presence of a base in a suitable solvent. Examples of the solvent are water, N,N-dimethylformamide, formamide, and dimethyl sulfoxide. As the base, alkali metal hydroxides such as sodium hydroxide can be exemplified. Preferably, the reaction system is maintained weakly basic. The reaction can be carried out at a temperature of, for example 0° to 100° C. for a period of, for example, 1 hour to about 1 week.

The protective groups can be split off as described with regard to process (a).

Compounds of formula (1) in which the 2'-position is H and the 4-position is a methylamino group ($R_3=H$) can be acylated, as desired, to convert it into the compounds of formula (1) in which $R_3$ is an acylamino group, in the same way as described above with regard to process (a).

The compounds of formula (1) in accordance with this invention which can be produced by any one of the processes (a), (b) and (c) can, if desired, be contacted with a pharmaceutically acceptable acid to convert them to their pharmaceutically acceptable said addition salts. The acid addition salt can be obtained by contacting the compound of formula (1) in free from with a suitable acid in accordance with means known per se. The desired addition salt can be obtained, for example, by adding a neutralizing amount, or an excessive amount, of an acid to the free compound of formula (1) in a solvent such as water or methanol, and then subjecting the reaction mixture to concentration to dryness, lyophilization, or precipitation with a solvent such as ethanol or dioxane.

Examples of the pharmaceutically acceptable acid are inorganic acids such as sulfuric acid, hydrochloric acid, hydrobromic acid, hydriodic acid, phosphoric acid, carbonic acid and nitric acid and organic acids such as acetic acid, fumaric acid, malic acid, citric acid, mandelic acid and succinic acid.

In the present invention, the compound of formula (1) that can be obtained from the compound of formula (2) in the above manner can be isolated and purified in a customary manner. Column chromatography is preferred. Preferred adsorbents for this purpose are cation exchange resins such as CM-Sephadex, Amberlite IRC-50, Amberlite IRC-84, Amberlite CG-50, and carboxymethyl cellulose. Development can be performed by a gradient method or a stepwise method using an alkaline aqueous solution such as an aqueous solution of ammonia or an aqueous solution of ammonium formate as a developing solvent. The active fractions are collected from the eluates, and lyophilized to obtain the compound of formula (1) in pure form.

The compounds of formula (1) exhibit superior antibiotic activity, and are useful as medicines for man and animals and also as intermediates for the synthesis of derivatives. The compounds of the invention are excellent also in that they have low toxicity.

Thus, the present invention can provide an antibiotic composition comprising the novel compound of formula (1).

Specifically, according to this invention, there is provided an antibiotic composition composed of (i) an antibiotically effective amount of a compound having the following formula (1)

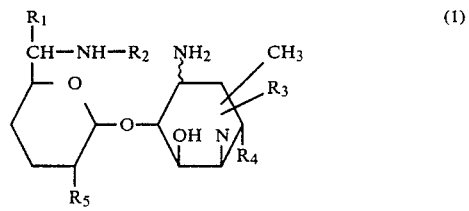

wherein each of $R_1$ and $R_2$ represents a hydrogen atom or a methyl group, $R_3$ represents a hydrogen atom or an amino-acyl group, $R_4$ represents a hydrogen atom or a hydroxyl or methoxy group, and $R_5$ represents a hydrogen atom or a hydroxyl group, or a pharmaceutically acceptable acid addition salt thereof, and (ii) pharmaceutically acceptable diluent or carrier.

The amount of the compound (1) is, for example, about 0.01 to about 99.5% by weight, based on the weight of the composition.

The antibiotic composition of this invention may be in any of the dosage forms usually employed, but injecting preparations and capsules are especially preferred.

Preferably, like known water-soluble basic antibiotics, an injectable is prepared by filling a lyophilized powder of the antibiotic into a vial, preferably together with a stabilizer, and in use, the contents of the vial are dissolved in a dissolving liquid for administration.

The diluent or carrier includes, for example, liquid diluents such as distilled water for injection and physiological isotonic solution, and solid carriers such as lactose, starch, white sugar, glucose, crystalline cellulose, calcium carbonate, kaolin, D-mannitol, magnesium metasilicate aluminate, calcium sulfate, calcium phosphate and bentonite. Addition of stabilizers such as acidic sodium bisulfite is also preferred.

The dosage of the antibiotic substance of this invention can be suitably selected, and is, for example, about 0.01 to about 100 mg/kg/day.

Thus, according to this invention, there can be provided antibiotic compositions for animals other than human, such as poultry, domesticated animals and cultivated fish, and antibiotic compositions for humans. These compositions are useful as antibacterial agents having a broad antibacterial spectrum.

Table 1 below summarizes the antibacterial spectra of several examples of the compound of formula (1) and starting materials therefor.

TABLE 1

|  | 2'-Deamino-2'-hydroxy-5-de-O—methyl-KA-6606 I | 2'-Deamino-5-de-O—methyl-KA-6606 I | 5-De-O—methyl-KA-6606 I (Starting compound) | 2'-Deamino-2'-hydroxy-5-demethoxy-KA-6606 I | 5-Demethoxy-KA-6606 I (Starting compound) |
|---|---|---|---|---|---|
| E. coli NIHJ JC-2 | 6.25 | 6.25 | 3.13 | 6.25 | 1.56 |
| K. pneumoniae PCI 602 | 1.56 | 0.78 | 0.78 | 1.56 | 0.78 |
| S. marcescens NHL | 3.13 | 0.78 | 0.78 | 1.56 | 0.78 |

TABLE 1-continued

| | 2'-Deamino-2'-hydroxy-5-de-O-methyl-KA-6606 I | 2'-Deamino-5-de-O-methyl-KA-6606 I | 5-De-O-methyl-KA-6606 I (Starting compound) | 2'-Deamino-2'-hydroxy-5-demethoxy-KA-6606 I | 5-Demethoxy-KA-6606 I (Starting compound) |
|---|---|---|---|---|---|
| P. inconstans 93 | 0.78 | 0.39 | 0.39 | 0.39 | 0.39 |
| P. vulgaris IID 874 | 6.25 | 6.25 | 3.13 | 3.13 | 1.56 |
| E. coli ML 1410 | 3.13 | 3.13 | 1.56 | 3.13 | 1.56 |
| E. coli ML 1410 R83 [APH(3')-II] | 6.25 | 3.13 | 1.56 | 6.25 | 1.56 |
| E. coli ML 1410 R102 [AAD(2'')] | 6.25 | 1.56 | 1.56 | 6.25 | 0.78 |
| K. pneumoniae 4687 [AAD(2'')] | 12.5 | 1.56 | 3.13 | 12.5 | 3.13 |
| E. coli ML 1410 R82 [AAD(3'')] | 3.13 | 1.56 | 1.56 | 3.13 | 1.56 |
| E. coli JR 88 [AAC(3)-I] | 1.56 | 3.13 | 12.5 | 1.56 | 12.5 |
| E. coli R176 [AAC(3)-II] | 6.25 | 1.56 | 3.13 | 3.13 | 3.13 |
| P. inconstans GN1554 [AAC(2')] | 6.25 | 1.56 | 1.56 | 3.13 | 1.56 |

The following Examples illustrate the present invention more specifically.

EXAMPLE 1

Production of 2'-deamino-5-de-O-methyl-2'-hydroxy-KA-6606II:

(A) 2.0 g of 5-de-O-methyl-KA-6606II (see U.S. Pat. No. 4,255,421) was dissolved in 60 ml of methanol, and 3.1 g of nickel acetate tetrahydrate was added. The mixture was stirred at room temperature for 30 minutes, and then cooled with ice. Then, 1.7 g of benzyloxycarbonyloxysuccinimide was added, and the mixture was stirred overnight. Concentrated aqueous ammonia (15 ml) was added to the reaction mixture, and the mixture was stirred for 1 hour and then concentrated to dryness. The residue was extracted with 100 ml of chloroform and 100 ml of water. The aqueous layer was separated, diluted with 100 ml of water, and absorbed on a column of Amberlite CG-50 ($NH_4^+$ form). The column was developed with 0.1–0.3N aqueous ammonia by a concentration gradient method. Fractions containing the desired product were collected and lyophilized to give 1.0 g of 2'-N-benzyloxycarbonyl-5-de-O-methyl-KA-6606II as a colorless powder.

Specific rotation: $[\alpha]_D^{23} = +145°$ (c 1, $H_2O$)

$^1H$—NMR: $\delta_{D_2O\ ppm}^{TMS\ (ext.)}$ (ext.: external standard)

1.51 (3H, d, J = 6.5 Hz, C—$CH_3$),
2.68 (3H, s, N—$CH_3$),
5.52 (1H, d, J = 3.5 Hz, H-1'), 5.58 (2H, s, $CH_2$—), 7.89 (5H, s, aromatic H).
Elemental analysis for $C_{22}H_{36}N_4O_6$:

| | C | H | N |
|---|---|---|---|
| Calculated (%) | 58.39 | 8.02 | 12.38 |
| Found (%) | 58.05 | 7.88 | 12.12 |

(B) The 2'-N-protected compound (800 mg) obtained in (A) above was dissolved in 20 ml of methanol, and 2 ml of acetic anhydride was added. The mixture was left to stand overnight at 37° C. The reaction mixture was concentrated to dryness and azeotroped with toluene to give 1.2 g of crude 1,4,6'-tri-N-acetyl-2'-N-benzyloxycarbonyl-5-de-O-methhyl-KA-6606II.

The product was dissolved in 15 ml of acetic acid, and catalytically reduced at room temperature and atmospheric pressure by adding 200 mg of 5% palladium carbon. After the reaction, the catalyst was removed by filtration. The filtrate was concentrated to dryness. The residue was chromatographed on a column of silica gel using the lower layer of chloroform-methanol-17% aqueous ammonia (2:1:1) as an eluent. Fractions containing the desired product were collected and concentrated to dryness to give 554 mg of 1,4,6'-tri-N-acetyl-5-de-O-methyl-KA-6606II as a colorless solid.

Specific rotation: $[\alpha]_D^{23} = +112°$ (c 1, $CH_3OH$)

$^1H$—NMR: $\delta_{D_2O\ ppm}^{TMS\ (ext.)}$ 1.61 (3H, d, J = 6.5 Hz, C—$CH_3$),
2.47, 2.49, 2.65 (each 3H, s, $COCH_3$),
3.65 (3H, s, N—$CH_3$),
5.42 (1H, d, J = 3.5 Hz, H-1').
Elemental analysis for $C_{20}H_{36}N_4O_7$:

| | C | H | N |
|---|---|---|---|
| Calculated (%) | 54.04 | 8.16 | 12.60 |
| Found (%) | 54.31 | 8.02 | 12.33 |

(C) The tri-N-protected compound (500 mg) obtained in (B) above was dissolved in 7 ml of water, and 7 ml of methanol was added. In an atmosphere of nitrogen, a solution of 284 mg of 3,5-di-t-butyl-o-benzoquinone in 7 ml of methanol was added dropwise, and the mixture was stirred overnight at room temperature. Oxalic acid dihydrate (184 mg) was added to the reaction mixture, and the mixture was stirred overnight at 45° C. Water (80 ml) was added to the reaction mixture, and the mixture was washed with benzene and concentrated to dryness. The residue was leached with 20 ml of methanol, and the leachate was concentrated to dryness to give 389 mg of 1,4,6'-tri-N-acetyl-2'-deamino-5-de-O-methyl-2'-oxo-KA-6606II. The product was dissolved in 9 ml of water, and 1.5 ml of methanol and 300 mg of sodium borohydride were added. The mixture was stirred at room temperature for 2 hours. One milliliter of acetic acid was added to the reaction mixture, and the mixture was concentrated to dryness to give crude 1,4,6'-tri-N-acetyl-2'-deamino-5-de-O-methyl-2'-hydroxy-KA-6606II. The product was dissolved in 10 ml of a 4N aqueous solution of sodium hydroxide, and reacted at 100° C. for 4 hours. The reaction mixture was neutralized with hydrochloric acid, diluted with 300 ml of water, and adsorbed on a column of Amberlite CG-50 ($NH_4^+$ form). The column was developed with 0.05–0.6N aqueous ammonia by a concentration gradient method. Fractions containing the desired product were collected and lyophilized to give 183 mg of 2'-deamino-5-de-O-methyl-2'-hydroxy-KA-6606II of the following formula as a colorless powder.

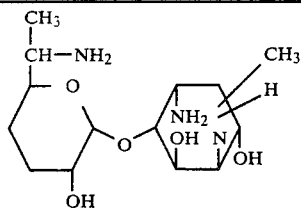

Specific rotation: $[\alpha]_D^{23} = +128°$ (c 2, $H_2O$)

$^1H$—NMR: $\delta_{D_2O\ ppm}^{TMS\ (ext.)}$ 1.53 (3H, d, J = 6.5 Hz, C—$CH_3$),
2.86 (3H, s, N—$CH_3$),
5.42 (1H, d, J = 3.5 Hz, H-1').
Elemental analysis for $C_{14}H_{29}N_3O_5 \cdot H_2O$:

|  | C | H | N |
|---|---|---|---|
| Calculated (%) | 49.83 | 9.26 | 12.45 |
| Found (%) | 49.51 | 9.03 | 12.11 |

EXAMPLE 2

Production of 2'-deamino-5-de-O-methyl-2'-hydroxy-KA-6606I:

(A) 122 mg of 2'-deamino-5-de-O-methyl-2'-hydroxy-KA-6606II obtained in Example 1 was dissolved in 3.8 ml of methanol, and 190 mg of nickel acetate tetrahydrate was added. The mixture was stirred at room temperature for 30 minutes. Then, 228 mg of benzyloxycarbonyloxysuccinimide was added, and the mixture was stirred for 2 hours. Concentrated aqueous ammonia (1.5 ml) was added to the reaction mixture and the mixture was stirred for 1 hour and then concentrated to dryness. The residue was dissolved in 30 ml of chloroform, washed with 3N aqueous ammonia and water, and dried. The solvent was evaporated to give 250 mg of crude 1,6'-bis-N-benzyloxycarbonyl-2'-deamino-5-de-O-methyl-2'-hydroxy-KA-6606II. The product was dissolved in 10 ml of dioxane, and 300 mg of an N-hydroxysuccinimide ester of N-benzyloxycarbonylglycine and 0.15 ml of triethylamine were added. They were reacted at 37° C. overnight. The solvent was evaporated from the reaction mixture, and the residue was chromatographed on a silica gel column using chloroform-methanol (16:1) as an eluent. Fractions containing the product were collected and concentrated to dryness to give 205 mg of tris-N-benzyloxycarbonyl-2'-deamino-5-de-O-methyl-2'-hydroxy-KA-6606I as a colorless solid.

Specific rotation: $[\alpha]_D^{24}$ +63° (c 1, $CHCl_3$)
IR: $\nu_{max}^{CHCl_3}$ cm$^{-1}$
1640 (amide I)
$^1H$—NMR: $\delta_{CDCl_3}$ ppm
1.03 (3H, d, J = 6.5 Hz, C—$CH_3$),
2.97 (3H, s, N—$CH_3$).
Elemental analysis for $C_{40}H_{50}N_4O_{12}$:

|  | C | H | N |
|---|---|---|---|
| Calculated (%) | 61.68 | 6.47 | 7.19 |
| Found (%) | 61.89 | 6.22 | 7.03 |

(B) The N-protected compound (205 mg) obtained in (A) above was dissolved in 2 ml of acetic acid, and 50 mg of palladium black was added. The compound was thus catalytically reduced at room temperature and atmospheric pressure. After the reaction, the catalyst was removed by filtration. The filtrate was diluted with 300 ml of water, neutralized with aqueous ammonia, and chromatographed on a column of CM-Sephadex C-25 ($NH_4^+$ form) using 0.05–0.5N aqueous ammonia by a concentration gradient method. Fractions containing the desired product were collected and lyophilized to give 82 mg of 2'-deamino-5-de-O-methyl-2'-hydroxy-KA-6606I of the following formula as a colorless powder.

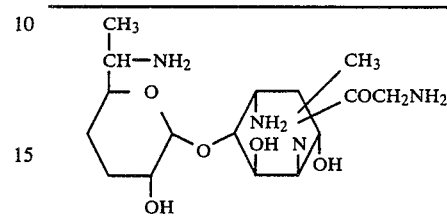

Specific rotation: $[\alpha]_D^{23} = +152°$ (c 0.5, $H_2O$)

$^1H$—NMR: $\delta_{D_2O\ ppm}^{TMS\ (ext.)}$ 1.52 (3H, d, J = 6.5 Hz, C—$CH_3$),
3.52 (3H, s, N—$CH_3$),
5.46 (1H, d, J = 3.5 Hz, H-1').
Elemental analysis for $C_{16}H_{32}N_4O_6 \cdot H_2O$:

|  | C | H | N |
|---|---|---|---|
| Calculated (%) | 48.72 | 8.69 | 14.20 |
| Found (%) | 48.48 | 8.41 | 13.98 |

EXAMPLE 3

Production of 2'-deamino-5-demethoxy-2'-hydroxy-KA-6606I:

(A) 6.3 g of 5-de-O-methyl-KA-6606II was dissolved in 200 ml of methanol, and 15 g of nickel acetate tetrahydrate was added. The mixture was stirred at room temperature for 30 minutes, and then 7.9 g of S-p-methoxybenzyloxycarbonyl-4,6-dimethyl-2-mercaptopyrimidine was added. The mixture was stirred overnight. Concentrated aqueous ammonia (70 ml) was added to the reaction mixture, and the mixture was stirred for 1 hour and concentrated to dryness. To the residue were added 250 ml of chloroform and 250 ml of water. The insoluble materials were removed by filtration, and the aqueous layer was separated. The chloroform layer was further extracted with water. The aqueous layers were combined and concentrated to dryness. The residue was chromatographed on a column of silica gel, using the lower layer of chloroform-methanol-17% aqueous ammonia (2:1:1) as an eluent. Fractions containing the desired product were collected and concentrated to dryness to give 2.4 g of 5-de-O-methyl-2'-N-(p-methoxybenzyloxycarbonyl)-KA-6606II as a colorless solid.

Specific rotation: $[\alpha]_D^{23} = +134°$ (c 1, $H_2O$)

$^1H$—NMR: $\delta_{D_2O\ ppm}^{TMS\ (ext.)}$ 1.44 (3H, d, J = 6.5 Hz, C—$CH_3$),
2.63 (3H, s, N—$CH_3$), 4.17 (3H, s, —⟨⟩—$OCH_3$).

Elemental analysis for $C_{23}H_{38}N_4O_7$:

|  | C | H | N |
|---|---|---|---|
| Calculated (%) | 57.24 | 7.94 | 11.61 |

| -continued |   |   |   |
|---|---|---|---|
| Found (%) | 57.01 | 7.66 | 11.35 |

(B) The 2'-N-protected compound (2.4 g) obtained in (A) above was dissolved in 24 ml of water, and with ice cooling, 2.4 g of sodium carbonate, 72 ml of methanol and 2.35 ml of carbobenzoxy chloride were added. The mixture was stirred at room temperature for 3 hours. The reaction mixture was concentrated to dryness. The residue was dissolved in chloroform, washed with water, and dried. The solvent was then evaporated to give crude 4.4 g of 1,4,6'-tris-N-benzyloxycarbonyl-5-de-O-methyl-2'-N-(p-methoxybenzyloxycarbonyl)-KA-6606II.

The crude product was dissolved in 98 ml of dioxane, and 98 ml of water and 3.1 g of barium hydroxide octahydrate were added. The mixture was stirred at 60° C. for 45 minutes. The reaction mixture was neutralized with dry ice, and 400 ml of methanol was added. The insoluble materials were removed by filtration. The filtrate was concentrated to dryness. The residue was dissolved in 200 ml of chloroform, washed with water and then dried. The solvent was evaporated. The residue was chromatographed on a column of silica gel using chloroform-methanol (20:1) as an eluent. Fractions containing the desired product were collected and concentrated to dryness to give 2.36 g of 1,6'-bis-N-benzyloxycarbonyl-3-0:4-N-carbonyl-5-de-O-methyl-2'-N-(p-methoxybenzyloxycarbonyl)-KA-6606II as a colorless solid.

Specific rotation: $[\alpha]_D^{24} = +31°$ (c 1, CHCl$_3$)
IR: $\nu_{max}^{CHCl_3}$ cm$^{-1}$
1765 (cyclic carbamate)
$^1$H—NMR: $\delta_{CDCl_3}$ ppm
1.05 (3H, d, J = 6.5 Hz, C—CH$_3$),
2.83 (3H, s, N—CH$_3$), 3.75 (3H, s, —⟨ ⟩—OCH$_3$).

Elemental analysis for C$_{40}$H$_{48}$N$_4$O$_{12}$:

|   | C | H | N |
|---|---|---|---|
| Calculated (%) | 61.84 | 6.23 | 7.21 |
| Found (%) | 61.58 | 6.12 | 7.05 |

(C) The carbamate compound (2.36 g) obtained in (B) above was dissolved in 45 ml of anhydrous methylene chloride, and 4.5 ml of anhydrous pyridine was added. The mixture was cooled to −10° C., and 1.88 ml of sulfuryl chloride was added. The mixture was left to stand overnight at the same temperature. The reaction mixture was added to a mixture of 250 ml of chloroform and 250 ml of a saturated aqueous solution of sodium hydrogen carbonate under cooling. The chloroform layer was separated, washed with a saturated aqueous solution of sodium hydrogen carbonate, and then dried. The solvent was evaporated, and the residue was dissolved in 50 ml of benzene. The solution was heated at 70° C. for 3 hours, and the solvent was evaporated. The residue was chromatographed on a column of silica gel using chloroform-methanol (50:1) as an eluent. Fractions containing the desired product were collected and concentrated to dryness to give 1.25 g of 1,6'-bis-N-benzyloxycarbonyl-3-0:4-N-carbonyl-5-chloro-5-demethoxy-2'-N-(p-methoxybenzyloxycarbonyl)-KA-6606II.

The product was dissolved in a mixture of 11 ml of anhydrous dioxane and 17 ml of anhydrous toluene, and in an atmosphere of nitrogen, 2.6 ml of tri-n-butyltin hydride and 30 mg of α,α'-azobisisobutyronitrile were added. The mixture was stirred at 80° C. for 3 hours. The solvent was evaporated from the reaction mixture. The residue was chromatographed on a column of silica gel using chloroform-methanol (60:1) as an eluent. Fractions containing the desired product were collected and lyophilized to give 0.88 g of 1,6'-bis-N-benzyloxycarbonyl-3-0:4-N-carbonyl-5-demethoxy-2'-N-(p-methoxybenzyloxycarbonyl)-KA-6606II as a colorless solid.

Specific rotation: $[\alpha]_D^{23} = -4.0°$ (c 1, CHCl$_3$)
IR: $\nu_{max}^{CHCl_3}$ cm$^{-1}$
1760 (cyclic carbamate)
$^1$H—NMR: $\delta_{CDCl_3}$ ppm
1.07 (3H, d, J = 6.5 Hz, C—CH$_3$),
2.72 (3H, s, N—CH$_3$), 3.88 (3H, s, —⟨ ⟩—OCH$_3$).

Elemental analysis for C$_{40}$H$_{48}$N$_4$O$_{11}$:

|   | C | H | N |
|---|---|---|---|
| Calculated (%) | 63.15 | 6.36 | 7.36 |
| Found (%) | 62.96 | 6.53 | 7.11 |

(D) The 5-demethoxy compound (630 mg) obtained in (C) was dissolved in 12 ml of a 0.5N p-toluenesulfonic acid-acetic acid solution, and 452 mg of anisole was added. The mixture was stirred at room temperature for 3 hours. The solvent was evaporated from the reaction mixture. The residue was dissolved in 60 ml of chloroform, and neutralized with 7 ml of 5% ammonia-methanol. The solution was washed with 1N sodium hydroxide and then with water, and dried. The solvent was then evaporated. The residue was chromatographed on a column of silica gel using chloroform-methanol-concentrated aqueous ammonia (120:10:1) as an eluent. Fractions containing the desired product were collected and concentrated to dryness to give 321 mg of 1,6'-bis-N-benzyloxycarbonyl-3-0:4-N-carbonyl-5-demethoxy-KA-6606II as a colorless solid.

Specific rotation: $[\alpha]_D^{22} = -19°$ (c 1, CHCl$_3$)
IR: $\nu_{max}^{CHCl_3}$ cm$^{-1}$
1760 (cyclic carbamate)
$^1$H—NMR: $\delta_{CDCl_3}$ ppm
1.07 (3H, d, J = 6.5 Hz, C—CH$_3$),
2.77 (3H, s, N—CH$_3$).
Elemental analysis for C$_{31}$H$_{40}$N$_4$O$_8$:

|   | C | H | N |
|---|---|---|---|
| Calculated (%) | 62.40 | 6.76 | 9.39 |
| Found (%) | 62.68 | 6.51 | 9.23 |

(E) The 2'-free amino compound (321 mg) obtained in (D) above was dissolved in 6 ml of methanol, and in an atmosphere of nitrogen, a solution of 143 mg of 3,5-di-t-butyl-o-benzoquinone in 6 ml of methanol was added dropwise, and the mixture was stirred overnight at room temperature. Water (2 ml) was added to the reaction mixture, and then 98 of oxalic acid dihydrate was added. The mixture was stirred overnight at 37° C. Chloroform (80 ml) was added to the reaction mixture, and the mixture was washed with water and dried. The solvent was evaporated. The residue was chromatographed on a column of silica gel using chloroform-methanol (30:1) as an eluent. Fractions containing the desired product were collected and concentrated to dryness to give 122 mg of 1,6'-bis-N-benzyloxycarbonyl-3-0:4-N-carbonyl-2'-deamino-5-demethoxy-2'-oxo-KA-6606II as a colorless solid.

The product was then dissolved in 5 ml of methanol, and 130 mg of sodium borohydride was added. The mixture was stirred at room temperature for 1.5 hours. Acetic acid (0.8 ml) was added to the reaction mixture, and the mixture was concentrated to dryness. The residue was dissolved in chloroform, washed with water and dried. The solvent was then evaporated. The residue was purified by preparative thin-layer chromatography [carrier: silica gel; developing solvent: chloroform-methanol (8:1)] to give 104 mg of 1,6'-bis-N-benzyloxycarbonyl-3-0:4-N-carbonyl-2'-deamino-5-demethoxy-2'-hydroxy-KA-6606II as a colorless solid.

Specific rotation: $[\alpha]_D^{22} = -22°$ (c 1, CHCl$_3$)
IR: $\nu_{max}^{CHCl_3}$ cm$^{-1}$
1755 (cyclic carbamate)
$^1$H—NMR: $\delta_{CDCl_2}$ ppm
1.06 (3H, d, J = 6.5 Hz, C—CH$_3$),
2.74 (3H, S, N—CH$_3$).
Elemental analysis for C$_{31}$H$_{39}$N$_3$O$_9$:

| | C | H | N |
|---|---|---|---|
| Calculated (%) | 62.30 | 6.58 | 7.03 |
| Found (%) | 62.56 | 6.31 | 7.18 |

(F) The 2'-hydroxy compound (104 mg) obtained in (E) above was dissolved in 1.75 ml of dioxane, and 1.75 ml of water and 248.5 mg of barium hydroxide octahydrate were added. The mixture was stirred at 60° C. for 16 hours. Dry ice was added to the reaction mixture and neutralized. Methanol was added, and the insoluble materials were removed by filtration. The filtrate was concentrated to dryness. The residue was dissolved in chloroform, washed with water and dried. The solvent was evaporated to give 58 mg of crude 1,6'-N-benzyloxycarbonyl-2'-deamino-5-demethoxy-2'-hydroxy-KA-6606II.

The product was then dissolved in 3 ml of dioxane, and 95 mg of an N-hydroxysuccinimide ester of N-benzyloxycarbonylglycine and 0.06 ml of triethylamine were added. The mixture was left to stand overnight at 37° C. The solvent was evaporated from the reaction mixture. The residue was purified by preparative thin-layer chromatography [carrier: silica gel; developing solvent: chloroform-methanol (6:1)] to give 65 mg of tris-N-benzyloxycarbonyl-2'-deamino-5-demethoxy-2'-hydroxy-KA-6606I as a colorless solid.

Specific rotation: $[\alpha]_D^{22} = +69°$ (c 1, CHCl$_3$)
IR: $\nu_{max}^{CHCl_3}$ cm$^{-1}$
1635 (amide I)
$^1$H—NMR: $\delta_{CDCl_3}$ ppm
1.05 (3H, d, J = 6.5 Hz, C—CH$_3$),
2.91 (3H, s, N—CH$_3$).
Elemental analysis for C$_{40}$H$_{50}$N$_4$O$_{11}$:

| | C | H | N |
|---|---|---|---|
| Calculated (%) | 62.98 | 6.61 | 7.34 |
| Found (%) | 62.66 | 6.42 | 7.13 |

(G) The N-protected compound (83 mg) obtained in (F) above was reacted and worked up in the same way as in Example 2, (B) to give 28 mg of 2'-deamino-5-demethoxy-2'-hydroxy-KA-6606I of the following formula as a colorless powder.

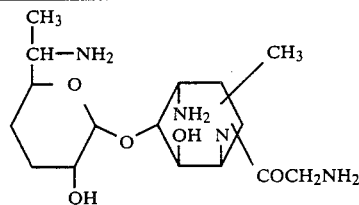

Specific rotation: $[\alpha]_D^{22} = +158°$ (c 1, H$_2$O)

$^1$H—NMR: $\delta_{D_2O\ ppm}^{TMS\ (ext.)}$ 1.53 (3H, d, J = 6.5 Hz, C—CH$_3$),
3.43 (3H, s, N—CH$_3$),
5.48 (1H, d, J = 3.5 Hz, H-1').
Elemental analysis for C$_{16}$H$_{32}$N$_4$O$_5$·H$_2$O:

| | C | H | N |
|---|---|---|---|
| Calculated (%) | 50.78 | 9.05 | 14.80 |
| Found (%) | 50.49 | 9.26 | 14.43 |

EXAMPLE 4

Production of 2'-deamino-5-de-O-methyl-KA-6606II:

(A) Hydroxylamine-O-sulfonic acid (2.4 g) was dissolved in a solution of 5 g of disodium phosphate dodecahydrate in 50 ml of water, and 1N sodium hydroxide was added to adjust the pH of the solution to 7.5. To the solution was added a solution of 500 mg of 1,4,6'-tri-N-acetyl-5-de-O-methyl-KA-6606II obtained in Example 1, (B) in 5 ml of water, and the mixture was heated in an atmosphere of nitrogen at 80° C. for 7 hours. The solvent was evaporated from the reaction mixture, and 30 ml of methanol was added to the residue to leach the product. The leachate was concentrated to dryness. The residue was chromatographed on a column of silica gel using chloroform-methanol (5:1) as an eluent. Fractions containing the desired product were collected and concentrated to dryness to give 226 mg of 1,4,6'-tri-N-acetyl-2'-deamino-5-de-O-methyl-KA-6606II as a colorless solid.

Specific rotation: $[\alpha]_D^{23} = +109°$ (c1, H$_2$O $^1$H—NMR: $\delta_{D_2O\ ppm}^{TMS\ (ext.)}$
1.54 (3H, d, J = 6.5Hz, C—CH$_3$),
2.45, 2.48, 2.63 (each 3H, s, COCH$_3$),
3.61 (3H, s, N—CH$_3$),
5.52 (1H, t, J$_{1',2'ax}$ = J$_{1',2'eq}$ = 3Hz, H—1').
Elemental analysis for C$_{20}$H$_{35}$N$_3$O$_7$:

| | C | H | N |
|---|---|---|---|
| Calculated (%) | 55.93 | 8.21 | 9.78 |
| Found (%) | 56.21 | 7.88 | 9.63 |

(B) The tri-N-protected compound (226 mg) obtained in (A) above was dissolved in 5 ml of a 4N aqueous solution of sodium hydroxide, and reacted at 100° C. for 5 hours. The reaction mixture was neutralized with hydrochloric acid, diluted with 150 ml of water, and charged on a column of Amberlite CG-50 (NH$_4^+$ form). The column was developed with 0.1–0.5N aqueous ammonia by a concentration gradient method. Fractions containing the desired product were collected and lyophilized to give 92 mg of 2'-deamino-5-de-O-methyl-KA-6606II of the following structural formula as a colorless powder.

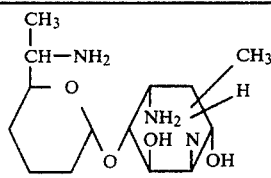

Specific rotation: $[\alpha]_D^{23} = +122°$ (cl, H$_2$O)

$^1$H—NMR: $\delta_{D_2O\ ppm}^{TMS\ (ext.)}$ 1.54 (3H, d, J = 6.5Hz, C—CH$_3$),
2.89 (3H, s, N—CH$_3$),
5.53 (1H, t, J$_{1',2'ax}$ = J$_{1',2'eq}$ = 3Hz, H—1').
Elemental analysis for C$_{14}$H$_{29}$N$_3$O$_4$.H$_2$O:

|  | C | H | N |
|---|---|---|---|
| Calculated (%) | 52.31 | 9.72 | 13.07 |
| Found (%) | 51.85 | 9.68 | 12.82 |

EXAMPLE 5

Production of 2'-deamino-5-de-O-methyl-KA-6606I:

(A) 82 mg of 2'-deamino-5-O-methyl-KA-6606II obtained in Example 4 was dissolved in 2.3 ml of methanol, and 137 mg of nickel acetate tetrahydrate was added. The mixture was stirred at room temperature for 30 minutes. Then, 137 mg of benzyloxycarbonyloxysuccinimide was added. The mixture was stirred for 2 hours, and 150 mg of benzyloxycarbonyloxysuccinimide was additionally charged. The mixture was stirred further for 2 hours, and 0.7 ml of concentrated aqueous ammonia was added. The mixture was stirred for one hour, and the solvent was evaporated from the reaction mixture. The residue was dissolved in 30 ml of chloroform, washed with 3N aqueous ammonia and water, and dried. The solvent was evaporated to give 153 mg of crude 1,6'-bis-N-benzyloxycarbonyl-2'-deamino-5-de-O-methyl-KA-6606II.

The crude product was dissolved in 6.8 ml of dioxane, and 225 mg of an N-hydroxysuccinimide ester of N-benzyloxycarbonylglycine and 0.14 ml of triethylamine were added. The mixture was stirred overnight at 37° C., and the solvent was evaporated from the reaction mixture. The residue was dissolved in 7 ml of methanol and 1.4 ml of concentrated aqueous ammonia. The solution was left to stand at room temperature for 2 hours. The solvent was evaporated. The residue was chromatographed on a column of silica gel using chloroform-methanol (20:1) as an eluent. Fractions containing the desired product were collected and concentrated to dryness to give 137 mg of tris-N-benzyloxycarbonyl-2'-deamino-5-de-O-methyl-KA-6606I as a colorless solid.

Specific rotation: $[\alpha]_D^{22} = +53°$ (cl, CHCl$_3$)

$^1$H—NMR: $\delta_{CDCl_3\ ppm}$
1.02 (3H, d, J = 6.5Hz, C—CH$_3$),
3.01 (3H, s, N—CH$_3$).
IR: $\nu_{max\ cm-1}^{CHCl_3}$ 1640 (amide I)
Elemental analysis for C$_{40}$H$_{50}$N$_4$O$_{11}$:

|  | C | H | N |
|---|---|---|---|
| Calculated (%) | 62.98 | 6.61 | 7.34 |
| Found (%) | 63.04 | 6.78 | 6.99 |

(B) The N-protected compound (137 mg) obtained in (A) above was dissolved in 2 ml of acetic acid, and 30 mg of palladium black was added. Thus, the compound was catalytically reduced at room temperature and atmospheric pressure. After the reaction, the catalyst was removed by filtration. The filtrate was diluted with 100 ml of water, neutralized with aqueous ammonia, and charged on a column of CM-Sephadex C-25 (NH$_4^+$ form). The column was developed with 0.1–0.5N aqueous ammonia by a concentration gradient method. Fractions containing the desired product were collected and lyophilized to give 47 mg of 2'-deamino-5-de-O-methyl-KA-6606I of the following structural formula as a colorless powder.

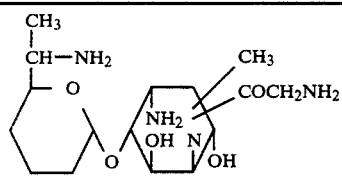

Specific rotation: $[\alpha]_D^{20} = +125°$ (cl, H$_2$O)

$^1$H—NMR: $\delta_{D_2O\ ppm}^{TMS\ (ext.)}$ 1.53 (3H, d, J = 6.5Hz, C—CH$_3$),
3.53 (3H, s, N—CH$_3$),
4.00 (2H, s, COCH$_2$NH$_2$),
5.57 (1H, t, J$_{1',2'ax}$ = J$_{1',2'eq}$ = 3Hz, H—1').
Elemental analysis for C$_{16}$H$_{32}$N$_4$O$_5$.H$_2$O:

|  | C | H | N |
|---|---|---|---|
| Calculated (%) | 50.78 | 9.05 | 14.80 |
| Found (%) | 50.33 | 8.86 | 14.55 |

EXAMPLE 6

Production of 2'-deamino-5-demethoxy-KA-6606II:

(A) 1.00 g of 5-demethoxy-KA-6606II (U.S. Pat. No. 4,353,893) was dissolved in 50 ml of methanol, and 2.5 g of nickel acetate tetrahydrate was added. The mixture was stirred at room temperature for 30 minutes. Then, 1.5 g of S-p-methoxybenzyloxycarbonyl-4,6-dimethyl-2-mercaptopyrimidine was added, and the mixture was stirred overnight at room temperature. The insoluble materials were removed by filtration from the reaction mixture, and 5 ml of concentrated aqueous ammonia was added to the filtrate. The mixture was stirred for 1 hour, and concentrated to dryness. The residue was leached with hot water, and the leachate was charged onto a column of CM-Sphadex C-25 (NH$_4^+$ form). The column was washed with water, and developed with 0.1N–0.5N aqueous ammonia by a concentration gradient method. Fractions containing the desired product were collected, concentrated and lyophilized to give 0.33 g of 5-demethoxy-2'-N-(p-methoxybenzyloxycarbonyl)-KA-6606II as a colorless solid.

Specific rotation: $[\alpha]_D^{22} = +94°$ (cl, H$_2$O)

$^1$H—NMR: $\delta_{10\%\ ND_3/D_2O\ ppm}^{TMS\ (int.)}$ (int.: internal standard)

1.03 (3H, d, J = 6.5Hz, C—CH$_3$),
2.15 (3H, s, N—CH$_3$), ~3.60 (H—2'),

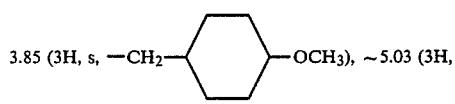

3.85 (3H, s, —CH$_2$—⟨⟩—OCH$_3$), ~5.03 (3H,

—CH₂—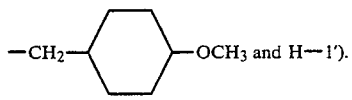—OCH₃ and H—1').

Elemental analysis for C₂₃H₃₈N₄O₆·½H₂CO₃·H₂O:

|  | C | H | N |
| --- | --- | --- | --- |
| Calculated (%) | 54.74 | 8.02 | 10.87 |
| Found (%) | 54.29 | 7.88 | 10.61 |

(B) The 2'-N-protected compound obtained in (A) above was N-acetylated in the same way as in Example 1, (B). The reaction mixture was concentrated to dryness, and the residue was azeotroped with toluene. The residue was purified by silica gel column chromatography [solvent: chloroform-methanol (20:1)] to give 374 mg of 1,4,6'-tri-N-acetyl-5-demethoxy-2'-N-(p-methoxybenzyloxycarbonyl)-KA-6606II as a colorless solid.

Specific rotation: $[\alpha]_D^{19} = +70°$ (c1, CHCl₃)

$^1$H—NMR: $\delta_{CDCl_3}$
1.12 (3H, d, J = 6.5Hz, C—CH₃),
1.83 (3H, s, N—COCH₃),
1.99 (6H, s, N—COCH₃),
2.96 (3H, s, N—CH₃), 3.79 (3H, s, —CH₂—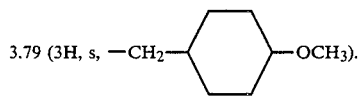—OCH₃).

Elemental analysis for C₂₉H₄₄N₄O₉:

|  | C | H | N |
| --- | --- | --- | --- |
| Calculated (%) | 58.77 | 7.48 | 9.45 |
| Found (%) | 58.92 | 7.24 | 9.40 |

(C) The 1,4,6'-N and 2'-N-protected compound (334 mg) obtained in (B) above was reacted and worked up in the same way as in Example 1, (B) to give 214 mg of 1,4,6'-tri-N-acetyl-5-demethoxy-KA-6606II as a colorless solid.

Specific rotation: $[\alpha]_D^{19} = +130°$ (c1, H₂O)

$^1$H—NMR: $\delta_{D_2O, ppm}^{TMS\ (int.)}$ 1.10 (3H, d, J = 6.5Hz, C—CH₃),
2.00, 2.03, 2.14 (each 3H, s, N—COCH₃),
3.08 (3H, s, N—CH₃),
4.94 (1H, d, J = 3.5Hz, H—1').

Elemental analysis for C₂₀H₃₆N₄O₆:

|  | C | H | N |
| --- | --- | --- | --- |
| Calculated (%) | 56.06 | 8.47 | 13.07 |
| Found (%) | 55.83 | 8.52 | 12.66 |

(D) The tri-N-protected compound (285 mg) obtained in (C) above was deaminated in the same way as in Example 4, (A). The reaction mixture was concentrated to dryness. The residue was leached with chloroform, and the leachate was concentrated to dryness. The residue was purified by silica gel column chromatography [solvent: chloroform-methanol (15:1)→(10:1)], and then lyophilized to give 120 mg of 1,4,6'-tris-N-acetyl-2'-deamino-5-demethoxy-KA-6606II.

Specific rotation: $[\alpha]_D^{19} = +98°$ (c1, H₂O)

$^1$H—NMR: $\delta_{D_2O}^{TMS\ (int.)}$
1.10 (3H, d, J = 6.5Hz, C—CH₃),
2.01, 2.20, 2.14 (each 3H, s, N—COCH₃),
3.06 (3H, s, N—CH₃),
5.08 (1H, br. s, H—1').

Elemental analysis for C₂₀H₃₅N₃O₆:

|  | C | H | N |
| --- | --- | --- | --- |
| Calculated (%) | 58.09 | 8.53 | 10.16 |
| Found (%) | 57.81 | 8.33 | 9.52 |

(E) The tris-N-protected-2'-N-deamino compound (100 mg) obtained in (D) above was reacted and worked up in the same way as in Example 4, (B) to give 86 mg of 2'-deamino-5-demethoxy-KA-6606II of the following structural formula as a colorless solid.

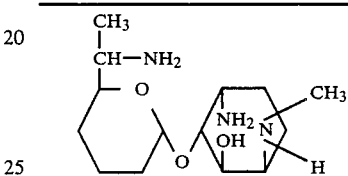

Specific rotation: $[\alpha]_D^{20} = +88°$ (c1, H₂O)

$^1$H—NMR: $\delta_{10\%\ ND_3/D_2O,\ ppm}^{TMS\ (int.)}$
1.03 (3H, d, J = 6.5Hz, C—CH₃),
2.33 (3H, s, N—CH₃),
5.10 (1H, br. s, H—1').

Elemental analysis for C₁₄H₂₉N₃O₃·H₂CO₃·H₂O:

|  | C | H | N |
| --- | --- | --- | --- |
| Calculated (%) | 49.03 | 9.05 | 11.44 |
| Found (%) | 49.30 | 8.82 | 10.97 |

EXAMPLE 7

Production of 2'-deamino-5-demethoxy-KA-6606I:

(A) The same procedure as described in the first half of Example 5, (A) was repeated using 61 mg of 2'-deamino-5-demethoxy-KA-6606II obtained in Example 6 to give 95 mg of crude 1,6'-bis-N-benzyloxycarbonyl-2'-deamino-5-demethoxy-KA-6606II.

The crude product was dissolved in 3 ml of acetonitrile, and 55 mg of N-benzyloxycarbonylglycine and 55 mg of dicyclohexylcarbodiimide were added. The mixture was stirred at room temperature for 2 hours. The insoluble materials were removed by filtration, and the filtrate was concentrated to dryness. The residue was chromatographed on a column of silica gel using chloroform-ethyl acetate (2:1→1:1) as an eluent. Fractions containing the desired product were collected and concentrated to dryness to give 49 mg of tris-N-benzyloxycarbonyl-2'-deamino-5-demethoxy-KA-6606I as a colorless solid.

Specific rotation: $[\alpha]_D^{19} = +55°$ (c1, CHCl₃)

$^1$H—NMR: $\delta_{CDCl_3,\ ppm}^{TMS}$
1.04 (3H, d, J = 6.5Hz, C—CH₃),
2.98 (3H, s, N—CH₃).
IR: $\nu_{max,\ cm^{-1}}^{CHCl}$
1640 (amide I)

Elemental analysis for C₄₀H₅₀N₄O₁₀:

|  | C | H | N |
| --- | --- | --- | --- |
| Calculated (%) | 64.33 | 6.75 | 7.50 |
| Found (%) | 64.13 | 6.68 | 7.24 |

(B) The N-protected compound (30 mg) obtained in (A) above was dissolved in 1.5 ml of 0.1N HCl-methanol, and hydrogenolyzed at room temperature and atmospheric pressure in the presence of a 5% palladium-carbon catalyst. The catalyst was removed from the reaction mixture by filtration, and the filtrate was concentrated to dryness under reduced pressure. The residue was charged on a column of CM-Sephadex C-25 ($NH_4^+$ form, a product of Pharmacia), and the column was developed with 0.1N–0.5N aqueous ammonia by a concentration gradient method. Fractions containing the desired product were collected and lyophilized to give 13 mg of 2'-deamino-5-demethoxy-KA-6606I of the following structural formula as a colorless solid.

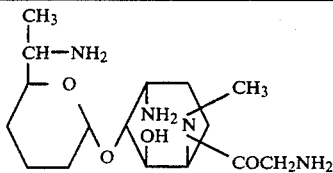

Specific rotation: $[\alpha]_D^{19} = +90°$ (cl, $H_2O$)

$^1H$—NMR: $\delta_{D_2O+DCl}^{TMS\,(int.)}$ ppm
1.33 (3H, d, J = 6.5Hz, C—$CH_3$),
3.03 (3H, s, N—$CH_3$),
4.04 (2H, s, —CO—$CH_2$—$NH_2$),
5.30 (1H, br. s, H—1').
Elemental analysis for $C_{16}H_{32}N_4O_4 \cdot H_2CO_3 \cdot H_2O$:

| | C | H | N |
|---|---|---|---|
| Calculated (%) | 48.10 | 8.55 | 13.19 |
| Found (%) | 48.32 | 8.56 | 12.77 |

EXAMPLE 8

Production of 2'-deamino-KA-7038III:

(A) Four hundred milligrams of KA-7038III was reacted and worked up in the same way as in Example 1, (A) to give 230 mg of 2'-N-benzyloxycarbonyl-KA-7038III as a colorless powder.

Specific rotation: $[\alpha]_D^{23}$ +75° (cl, $H_2O$)

$^1H$—NMR: $\delta_{D_2O}^{TMS\,(ext.)}$, ppm
2.71 (3H, s, N—$CH_3$),
2.86 (3H, s, N—$CH_3$),
3.93 (3H, s, N—$CH_3$),

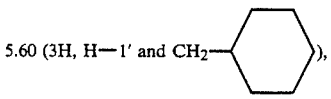

5.60 (3H, H—1' and $CH_2$—), 7.88 (5H, s, aromatic H).
Elemental analysis for $C_{23}H_{38}N_4O_6 \cdot H_2O$:

| | C | H | N |
|---|---|---|---|
| Calculated (%) | 57.01 | 8.32 | 11.56 |
| Found (%) | 56.53 | 8.28 | 11.25 |

(B) The 2'-N-protected compound (220 mg) obtained in (A) above was reacted and worked up in the same way as in Example 1, (B) to give 182 mg of 1,4,6'-tri-N-acetyl-KA-7038III as a colorless solid.

Specific rotation: $[\alpha]_D^{22} = +63°$ (cl, $CH_3OH$)

$^1H$—NMR: $\delta_{D_2O,\,ppm}^{TMS\,(ext.)}$
2.44, 2.46, 2.62 (each 3H, s, $COCH_3$),
3.41, 3.52 (3H in total, s, N—$CH_3$, rotomers),
3.60, 3.63 (3H in total, s, N—$CH_3$, rotomers),
3.86, 3.87 (3H in total, s, O—$CH_3$, rotomers).
Elemental analysis for $C_{21}H_{38}N_4O_7$:

| | C | H | N |
|---|---|---|---|
| Calculated (%) | 55.00 | 8.35 | 12.22 |
| Found (%) | 54.87 | 8.48 | 12.07 |

(C) The 2'-N-free compound (175 mg) obtained in (B) above was reacted and worked up in the same way as in Example 4, (A) to give 82 mg of 1,4,6'-tri-N-acetyl-2'-deamino-KA-7038III as a colorless solid.

Specific rotation: $[\alpha]_D^{23} = +59°$ (cl, $H_2O$)

$^1H$—NMR: $\delta_{CDCl_3}^{TMS}$
2.46, 2.48, 2.60 (each 3H, s, $COCH_3$),
3.43, 3.52, 3.58, 3.62 (6H in total, s, N—$CH_3$, rotomers),
3.90, 3.92 (3H, s, O—$CH_3$, rotomers).
Elemental analysis for $C_{21}H_{37}N_3O_7$:

| | C | H | N |
|---|---|---|---|
| Calculated (%) | 56.87 | 8.41 | 9.47 |
| Found (%) | 56.81 | 8.62 | 9.18 |

(D) The 2'-deamino compound (80 mg) obtained in (C) above was reacted and worked up in the same way as in Example 4, (B) to give 31 mg of 2'-deamino-KA-7038III of the following structural formula as a colorless solid.

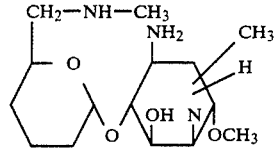

Specific rotation: $[\alpha]_D^{22}$ +73° (cl, $H_2O$)

$^1H$—NMR: $\delta_{D_2O}^{TMS\,(ext.)}$ 2.84, 2.86 (each 3H, s, N—$CH_3$),
3.93 (3H, s, O—$CH_3$),
5.60 (1H, br. s, H—1').
Elemental analysis for $C_{15}H_{31}N_3O_4 \cdot 2H_2O$:

| | C | H | N |
|---|---|---|---|
| Calculated (%) | 50.97 | 9.98 | 11.89 |
| Found (%) | 50.23 | 9.86 | 11.71 |

EXAMPLE 9

Production of 2'-deamino-KA-7038I:

(A) The 2'-deamino-KA-7038III (28 mg) obtained in Example 8 was reacted and worked up in the same way as in Example 5 to give 41 mg of tris-N-benzyloxycarbonyl-2'-deamino-KA-7038I as a colorless solid.

Specific rotation: $[\alpha]_D^{23}$ +36° (cl, $CHCl_3$)

$^1H$—NMR: $\delta_{CDCl_3}$, ppm
2.93 (6H, s, N—$CH_3$)
Elemental analysis for $C_{41}H_{52}N_4O_{11}$:

| | C | H | N |
|---|---|---|---|
| Calculated (%) | 63.39 | 6.75 | 7.21 |
| Found (%) | 63.18 | 6.75 | 6.93 |

(B) The tris-N-protected compound (30 mg) obtained in (A) above was reacted and worked up in the same way as in Example 5, (B) to give 11 mg of 2'-deamino-KA-7038I of the following structural formula as a colorless solid.

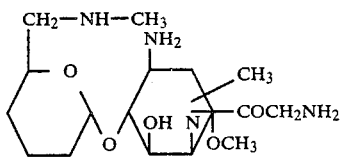

Specific rotation: $[\alpha]_D^{22} = +102°$ (c 0.5, H$_2$O)

$^1$H—NMR: $\delta_{D_2O}^{TMS\ (ext.)}$
3.80, 3.53 (each 3H, s, N—CH$_3$),
3.91 (3H, s, O—CH$_3$),
4.07 (2H, s, —CO—CH$_2$—NH$_2$),
5.47 (1H, br. s, H—1').
Elemental analysis for C$_{17}$H$_{34}$N$_4$O$_5$.H$_2$CO$_3$.H$_2$O:

|  | C | H | N |
|---|---|---|---|
| Calculated (%) | 47.56 | 8.43 | 12.33 |
| Found (%) | 46.86 | 8.41 | 12.06 |

Pharmaceutical Production Example

One hundred grams of the compound obtained in Example 2 was dissolved in 1000 ml of distilled water, and the pH of the solution was adjusted to 6.0 with sulfuric acid. The solution was then aseptically filtered, filled in 500 vials for injections in an amount of 2 ml for each, and lyophilized to obtain final products. In use, they are dissolved in distilled water for injection.

What is claimed is:

1. An aminoglycoside represented by the following formula (1)

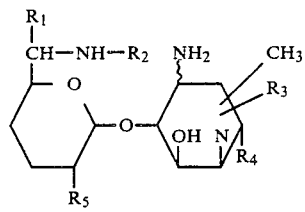

wherein each of R$_1$ and R$_2$ represents a hydrogen atom or a methyl group, R$_3$ represents a hydrogen atom or an aminoacyl group having 2 to 4 carbon atoms in the acyl group, R$_4$ represents a hydrogen atom or a hydroxyl or methoxy group, and R$_5$ represents a hydrogen atom or a hydroxyl group, or a pharmaceutically acceptable acid addition salt thereof.

2. An antibiotic composition which comprises
   (i) an antibiotically effective amount of a compound having the following formula (1)

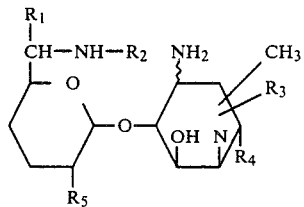

wherein each of R$_1$ and R$_2$ represents a hydrogen atom or a methyl group, R$_3$ represents a hydrogen atom or an aminoacyl group having 2 to 4 carbon atoms in the acyl group, R$_4$ represents a hydrogen atom or a hydroxyl or methoxy group, and R$_5$ represents a hydrogen atom or a hydroxyl group, or a pharmaceutically acceptable acid addition salt thereof, and
   (ii) a pharmaceutically acceptable diluent or carrier.

3. The antibiotic composition of claim 2 wherein the amount of the compound of formula (1) or its pharmaceutically acceptable acid addition salt is about 0.01 to about 99.5% by weight based on the weight of the composition.

* * * * *